(12) United States Patent
Ortiz-Marciales et al.

(10) Patent No.: US 7,109,345 B1
(45) Date of Patent: Sep. 19, 2006

(54) EFFICIENT AND CONVENIENT PROCEDURE FOR THE SYNTHESIS OF B-ALKYLATED OXAZABOROLIDINES DERIVED FROM EPHEDRINE AND NOREPHEDRINE

(76) Inventors: Margarita Ortiz-Marciales, Department of Chemistry, University of Puerto Rico, CUH Station, Humacao, PR (US) 00791; Melvin de Jesús, Department of Chemistry, University of Puerto Rico, Humacao, PR (US) 00791; Eduvigis Gonzalez, Department of Chemistry, University of Puerto Rico, Humacao, PR (US) 00791; Sandraliz Espinosa, P.O. Box 8851, Humacao, PR (US) 00791; Wildeliz Correa-Ramirez, Department of Chemistry, University of Puerto Rico, Humacao, PR (US) 00791

( * ) Notice: Subject to any disclaimer, the term of this patent is extended or adjusted under 35 U.S.C. 154(b) by 386 days.

(21) Appl. No.: 10/775,011

(22) Filed: Feb. 9, 2004

Related U.S. Application Data

(60) Provisional application No. 60/445,743, filed on Feb. 7, 2003.

(51) Int. Cl.
*C07D 263/04* (2006.01)
(52) U.S. Cl. .................................... 548/110
(58) Field of Classification Search ................. 548/110
See application file for complete search history.

(56) References Cited

U.S. PATENT DOCUMENTS

| | | | |
|---|---|---|---|
| 6,005,133 | A | 12/1999 | Quallich |
| 6,020,495 | A | 2/2000 | Sun et al. |
| 6,037,505 | A | 3/2000 | Quallich |
| 2002/0038053 | A1 | 3/2002 | Draper |

OTHER PUBLICATIONS

Shinichi Itsuno, Koichi Ito, Akira Hirao and Seiichi Nakahama; Asymmetric Reduction of Aliphatic Ketones with The Reagent Prepared from (S)-(-)-2-Amino-3-methyl-1, 1-diphenylbutan-1-Ol And Borane; *J. Org. Chem.*; 1984; pp. 555-557; School of Materials Science, Toyohashi, Japan; Department of Polymer Science, Tokyo, Japan.

Elias J. Corey and Christopher J. Helal; Reduction of Carbonyl Compounds with Chiral Oxazaborolidine Catalysts; A New Paradigm for Enantioselective Catalysis and a Powerful New Synthetic Metod; *Angewandte Chemie*; 1988; pp. 1986-2012; Germany.

Yoji Sakito, Yukio Yoneyoshi, and Gohfu Suzukamo; Asymmetric Reduction of Oxime Ethers, Distinction of Anti and Syn Isomers Leading to Enantiomeric Amines; *Tetrahedron Letters*, 1988; pp. 223-224; Great Britain.

N. N. Joshi, M. Srebnik, and Herbert C. Brown; Chiral Oxazaborolidines as Catalysts for the Enantioselective Addition of Diethyizinc to Aldehydes; *Tetrahedron Letters*; 1989; pp. 5551-5554; Great Britain.

John M. Brown and Guy C. Lloyd-James; Catalytic Asymmetric Hydroboration with Oxazaborolidines; *Tetrahedron: Asymmetry*; 1990; pp. 869-872; Great Britain.

Vinod K. Singh; Practical and Useful Methods for Enantioselective Reduction of Unsymmetrical Ketones; *Review*; Indian Institute of Technology; 1991; pp. 605-617; India.

Laurent Deloux and Morris Srebnik; Asymmetric Boron-Catalyzed Reactions; *Chem. Rev.*; 1992; pp. 763-784; University of Toledo, Ohio, USA.

Byung Tae Cho and Yu Sung Chun; Asymmetric Borane Reduction of Achiral Ketones Mediated by a Chiral Oxazaborolidine Derieved from (-)-Ephedrine; *Tetrahedron: Asymmetry*; 1992; pp. 1539-1542; Great Britain.

Sabine Wallbaum and Jürgen Martens; Asymmetric Syntheses with Chiral Oxazaborolidines; *Tetrahedron: Asymmetry*; 1992; pp. 1475-1504; Great Britain.

P. Y. Chavant and M. Vaultier; Preparation of some organo-bis (diisopropylamino) boranes and their Application to the Synthesis of Oxazaborolidines; *Journal of Organometallic Chemistry*; 1992; pp. 37-46; France.

D. J. Mathre, Andre S. Thompson, Alan W. Douglas, Karst Hoosteen, James D. Carroll, Edward G. Corely, and Edward J. J. Grabowski; A Practical Process for the Preparation of Hydro-1-methil-3,3-diphenyl-1H,3H-pyrrolo[1,2-c]-oxazaborole-borane. A Highly Enantioselective Stoichiometric and Catalyctic Reducing Agent; *J. Org. Chem*; 1993; pp. 2880-2888; New Jersey, USA.

John M. Brown, Guy C. Lloyd-Jones, and Timothy P. Layzell; Reversible Dimerisation of Ephedrine-derived Oxazaborolidines ; Tetrahedron: Asymmetry; 1993; pp. 2151-2154; Great Britain.

Masako Nakagawa, Tomohiko Kawate, Taro Kakikawa, Hideki Yamada, Teruaki Matsui, and Tohru Hino; Asymmetric Reductions of Imines and Ketones by Chiral Oxaborolidines; *Tetrahedron: Asymmetry*; 1993; pp. 1739-1748; Chiba University; Japan; Great Britain.

Ramon Berenguer, Jordi Garcia, and Jaume Vilarrasa; Selective Reduction of Ketones Catalysed by Oxazaborolidines Prepared from Phenylglycine; *Tetrahedron: Asymmetry*; 1994; pp. 165-168; University of Barcelona, Spain; Great Britain.

Vesa Nevalainen; Quantum Chemical Modeling of Chiral Catalysis. Part 16. On the Isomerism of Dimers of Chiral Oxazaborolidines used in the Catalytic Enantioselective Reduction of Ketones.; *Tetrahedron: Asymmetry*; 1994; pp. 387-394; University of Helsinki, Finland; Great Britain.

(Continued)

*Primary Examiner*—Kamal A. Saeed
*Assistant Examiner*—Michael P. Barker
(74) *Attorney, Agent, or Firm*—Hoglund & Pamias PSC; Heath W. Hoglund

(57) ABSTRACT

A novel and efficient alkylation procedure of B—H-1,3,2-oxazaborolidines derived from ephedrine and norephedrine has been established. Representative B-butyl- and B-methyl-1,3,2-oxazaborolidines were prepared in good yield and excellent purity by one pot treatment of the parent borahet-erocyclic compound with the corresponding organolithium reagent and subsequent hydrolysis of the cyclic borohydride with anhydrous ammonium chloride.

14 Claims, 5 Drawing Sheets

OTHER PUBLICATIONS

George J. Quallich, James F. Blake, and Teresa M. Woodall; Oxazaborolidines Structure and Enantioselectivity Relationships; *J. Am. Chem. Soc.*; 1994; pp. 8516-8525; USA.

Byung Tae Cho, Yu Sung Chun, Ch. Dauelsberg, Sabine Wallbaum, and Jürgen Martens; Catalytic Enantioselective Reactions. Part 2. A Comparison Study of Asymmetric Borane Reduction of Prochiral Ketones Catalyzed by Chiral Oxazaborolidines; *Communications to the Editor*; 1994; pp. 101-103; Germany.

Byung Tae Cho, Mi Hae Ryu, Yu Sung Chun, Ch. Dauelsberg, Sabine Wallbaum, and Jürgen Martens; A Direct Comparison Study of Asymmetric Borane Reduction of C=N Double Bond Mediated by Chiral Oxazaborolidines; *Bull. Korean Chem. Soc.*, 1994: pp. 53-57; Republic of Korea/Germany.

E. J. Corey and Karlene A. Cimprich; Highly Enantioselective Alkynylation of Aldehydes Promoted by Chiral Oxazaborolidines; *J. Am. Chem. Soc.*; 1994; pp. 3151-3152; USA.

Claude Caze, Noureddine El Moualij, Philip Hodge, Christopher J. Lock, and Jianbiao Ma; Some Enantioselective Borane Reductions of Prochiral Ketones Catalysed by Polymer-supported Oxazaborolidines Bound via the Boron Atom; *J..Chem. Soc. Perkin Trans.*; 1995; pp. 345-349; France/United Kingdom.

Jordi Bach, Ramon Berenguer, Jordi Garcia, Teresa Loscertales, and Jaume Vilarrasa; Highly Enantioenriched Propargylic Alcohols by Oxazaborolidine-Mediated Reduction of Acetylenic Ketones; *J. Org. Chem.*; 1996; pp. 9021-9025; Spain/USA.

Ahmed F. Abdel-Magid; Reductions in Organic Synthesis. Recent Advances and Practical Applications; American Chemical Society; 1996; pp. 112-126; USA.

John T. Dougherty, Joseph R. Flisak, Jerome Hayes, Ivan Lantos, Li Liu, and Lynn Tucker; Asymmetric reduction of ketoxime ethers to optically active O-substituted hydroxylamines with reagents prepared from borane and chiral amino alcohols; *Tetrahedron: Asymmetric*; 1997; pp. 497-499; Great Britain.

Byung Tae Cho, and Yu Sung Chun; Facile Synthesis of Terminal 1,2-Diols with High Optical Purity via Oxazaborolidine-Catalyzed Asymmetric Borane Reduction; *J. Org. Chem.*; 1998; pp. 5280-5282; USA.

Alberto Rosendo Rico, Margarita Tlahuextl, Angelina Flores-Parra, Rosalinda Contreras; Addition reactions of protonic reagents to optically active 2-phenyl-1,3,2-oxazaborolidines; *Journal of Organometallic Chemistry*; 1998; pp. 122-128; México/USA.

Cristina Puigjaner, Anton Vidal-Ferran, Albert Moyano, Miquel A. Pericas, and Antoni Riera; A New Family of Modular Chiral Ligands for the Catalytic Enantioselective Resuction of Prochiral Ketones; *J. Org. Chem.*, 1999; pp. 7902-7911; Spain/USA.

Evelyne Fontaine, Claudie Namane, Jerome Meneyrol, Michel Geslin, Laurence Serva, Eliane Roussey, Stephanie Tiessandie, Mohamed Maftouh, and Pierre Roger; Synthesis of optically-active benzylic amines; asymmetric reduction of ketoxime ethers with chiral oxazaborolidines; *Tetrahedron: Asymmetry*; 2001; pp. 2185-2189; France/USA.

Akira Hirao, Shinichi Itsuno, Seiichi Nakahama, Noboru Yamazaki; Asymmetric Reduction of Aromatic Ketones with Chiral Alkoxyamine-borane Complexes; *J.C.S. Chem. Comm*; 1981; pp. 315-317; US.

Jean-Paul G. Seerden, Mike M.M. Boeren, Hans W. Scheeren; 1,3-Dipolar Cycloaddition Reactions of Nitrones with Alkyl Vinyl Ethers Catalyzed by Chiral Oxazaborlidines; *Tetrahedron*, vol. 53; 1997; pp. 11843-11852; US.

George J. Quallich, James F. Blake, Teresa M. Woodall; Diphenyloxazaborolidine for Enantioselective Reduction of Ketones; *American Chemical*; 1996; pp. 112-126; US.

Byung Tae Cho, Mi Hae Ryu; Asymmetric Borane Reduction of Ketoxime O-Trimethylsilyl Ethers Mediated by a Chiral 1,3,2-Oxazaborolidine Derived from (-),Ephedrine; *Bull. Korean Chem. Soc.*; 1994; pp. 191-192; US.

John M. Brown, Guy C. Lloyd-Jones; Vinylborane Formation in Rhodium-catalysed Hydroborations; Ligand-free Homogeneous Catalysis; *J. Chem. Soc., Chem. Commun.* ; 1992; pp. ; US.

Byung Tae Cho, Yu Sung Chun; Catalytic Enantioselective Reactions. Part 10. Enantioselective Addition of Diethylzinc to Aldhydes Catalyzed by Chiral Oxazaborolidenes; Bull. Korean Chem. Soc.; 1996; pp. 1096-1098; US.

EFFICIENT AND CONVENIENT PROCEDURE FOR THE SYNTHESIS OF B-ALKYLATED OXAZABOROLIDINES DERIVED FROM EPHEDRINE AND NOREPHEDRINE

CLAIM OF PRIORITY

This application claims the benefit of U.S. Provisional Application No. 60/445,743, filed Feb. 7, 2003, which is incorporated herein by reference in its entirety.

FEDERAL GRANTS

This research was supported, in part, by the National Institute of Health through their MBRS (GM 08216) and NIH-AREA (GM 59829) grants. The Government has certain rights in this invention.

BACKGROUND OF THE INVENTION

Chiral 1,3,2-oxazaborolidines have been well studied and regarded as important catalysts or reagents for the enantioselective reduction of prochiral ketones, imines and oximes, and in other stereoselective transformations. The development of oxazaborolidines has been driven mainly by the availability of suitable chiral aminoalcohols. Norephedrine and ephedrine are commercially available and relatively inexpensive in the two enantiomeric forms, and their derived oxazaborolidines have been reported as efficient chiral templates for the borane reduction of prochiral ketones and C=N double bonds, in catalytic hydroborations, as well as in additions of diethylzinc to aldehydes.

B—H oxazaborolidines are usually prepared by the reaction of norephedrine or ephedrine with borane-THF or borane dimethylsulfide complex. Their extreme sensitivity to air and moisture make these reagents difficult to purify by distillation or recrystallization and, consequently, they are commonly prepared in situ for subsequent reactions. However, side products present with the unpurified B—H heterocyclic catalysts or reagents cause a detrimental effect on the enantiomeric purity of desired chiral products. Furthermore, B—H oxazaborolidines can form dimers that alter the nature of the chiral catalyst. On the contrary, B-alkylated compounds are more stable, easier to purify and handle than the nonsubstituted counterparts, and produce similar enantioselectivities. B-substituted 1,3,2-oxazaborolidines are typically prepared by condensation of the aminoalcohols with boronic acids, boroxines, or their boronate esters, by removing water and boronic acid, or boronic ester residues, by azeotropic distillation in toluene. The treatment of chiral aminoalcohols with organo-bis(diisopropylamino)borane for the synthesis of B-alkyl and phenyl oxazaborolidines has also been reported. However, these methods require expensive and elaborated reagents, and moreover, the complete removal of water and boronic acid, or it derivatives, is extremely difficult.

Such methods are disclosed by and through the following references, each of which are incorporated herein by reference in their entirety:

1. Hirao, A.; Itsuno, S.; Nakahama, S.; Yamazaki, Y. *J. Chem. Soc., Chem. Commun.* 1981, 1315–1317.
2. Corey, E. J.; Helal, C. J. *Angew. Chem. Int. Ed.* 1998, 37, 1986–2012.
3. Deloux, L.; Srebnik, M. *Chemical Reviews* 1993, 93, 763–784.
4. Singh, V. K. *Synthesis* 1992, 605–617.
5. Wallbaum, S.; Martens, J. *Tetrahedron: Asymm.* 1992, 3, 475–1504.
6. Nakagawa, M.; Kawate, T.; Kakikawa, T.; Yamada, H.; Matsui, T.; Hino, T. *Tetrahedron* 1993, 49, 1739–1748.
7. Fontaine, E.; Namane, C.; Meneyrol, J.; Geslin, M.; Serva, L.; Roussey, E.; Tissandie, S.; Maftouh, M.; Roger, P. *Tetrahedron: Asymm.* 2001, 12, 2185–2189.
8. Puigjaner, C. V.-F., A.; Moyano, A.; Pericas, M. A.; Riera, A. *J. Org. Chem.* 1999, 64, 7902–7911.
9. Seerden, J.-P. G. B., Mike M. M.; Scheeren, H. W. *Tetrahedron* 1997, 53, 11843–11852.
10. Corey, E. J.; Cimprich, K. A. *J. Am. Chem. Soc.* 1994, 116, 3151–3152.
11. Joshi, N. N.; Srebnik, M.; Brown, H. C. *Tetrahedron Lett.* 1989, 30, 5551–5554.
12. Brown, J. M.; Lloyd-Jones, G. C. *Tetrahedron: Asymm.* 1990, 1, 869–872.
13. Caze, C.; El-Moualij, N.; Hodge, P.; Lock, C. J.; Ma, J. *J. Chem. Soc., Perkin Trans.* 1 1995, 345–349.
14. Cho, B. T.; Chun, Y. S. *Tetrahedron Asymm.* 1992, 3, 1539–1542.
15. Berenguer, R.; Garcia, J.; Vilarrasa, J. *Tetrahedron: Assymm.* 1994, 5, 165–168.
16. Bach, J.; Berenguer, R.; Jordi Garcia, J.; Loscertales, T.; Vilarrasa, J. *J. Org. Chem.* 1996, 61, 9021–9025.
17. Quallich, G. J. Blake, J. F.; Woodall, T. M. In *Reductions in Organic Synthesis*; Abdel-Magid, A. F., Ed. Diphenyloxazaborolidines for Enantioselective Reduction of Ketones. American Chemical Society: Washington, D.C., 1996, Chap. 7, pp. 112–126.
18. Quallich, G. J. B., James F.; Woodall, Teresa M. *J. Amer. Chem. Soc.* 1994, 116, 8516–8525.
19. Cho, T. B.; Ryu, M. H. *Bull Korean Chem. Soc.* 1994, 15, 191–192.
20. Cho, B. T.; Ryu, M. H.; Chun, Y. S.; Dauelsberg, C.; Wallbaum, S.; Martens, J. *Bull. Korean Chem. Soc.* 1994, 15, 53–57.
21. Dougherty, J. T.; Flisak, J. R.; Hayes, J.; Lantos, I.; Liu, L.; Tucker, L. *Tetrahedron Asymmetry* 1997, 8, 497–500.
22. Brown, J. M.; Lloyd-Jones, G. C. *J. Chem. Soc., Chem. Commun.* 1992, 710–713.
23. Cho, B. T.; Chun, Y. S. *Bull. Korean Chem. Soc.* 1996, 17, 1096–1098.
24. Sakito, Y.; Yoneyoshi, Y.; Suzukamo, G. *Tetrahedron Lett.* 1988, 29, 223–224.
25. Mathre, D. J.; Thompson, A. S.; Douglas, A. W.; Hoogsteen, K.; Carroll, J. D.; Corley, E. G.; Grabowski, E. J. J. *J. Org. Chem.* 1993, 58, 2880–2888.
26. Nevalainen, V. *Tetrahedron Asymm.* 1994, 5, 387–394.
27. Chavant, P. Y. V., M. *J. Organometallic Chem.* 1993, 455, 37–46.
28. Ortiz-Marciales, M.; González, E.; Figueroa, R.; Martínez, J.; Muñoz, X. Sandraliz, E.; Correa W., Presentation 820, Chem. Ed. Section, 223$^{rd}$ ACS National Meeting, Orlando, Fl., Apr. 8, 2002.
29. B-phenyl boronic acid intermediates formed by the addition of water to oxazaborolidines were reported by Rico, A. R.; Tlahuextl, M.; Flores-Parra, A.; Contreras, R. *J. Organomet. Chem.* 1999, 581, 122–128.
30. Quallich, G. J. U.S. Pat. No. 6,037,505, May 14, 2000.
31. Quallich, G. J. U.S. Pat. No. 6,005,133, Dec. 21, 1999.
32. Draper, R. W. U.S. Patent Publication Doc. No. 2002/0038053 A 1, Mar. 28, 2002, "4-Cyclohexyl-1,3,2-oxazaborolidine Chiral."
31. Ortiz-Marciales, M.; de Jesús, M.; González, E.; Espinosa, S.; Correa-Ramírez, W.; U.S. Provisional Application No. 60/445,743, filed Feb. 7, 2003.

SUMMARY OF THE INVENTION

Pure B-alkyl-1,3,2-oxazaborolidines are derived from ephedrine and norephedrine via alkylation of the parent boraheterocyclic compound. According to one aspect of the invention, the reaction is performed by means of a one-pot synthesis. A preferred method is shown in FIG. 1, where R=H or Me and $R^1$=Me or n-Bu.

DETAILED DESCRIPTION OF THE INVENTION

Figure 2:
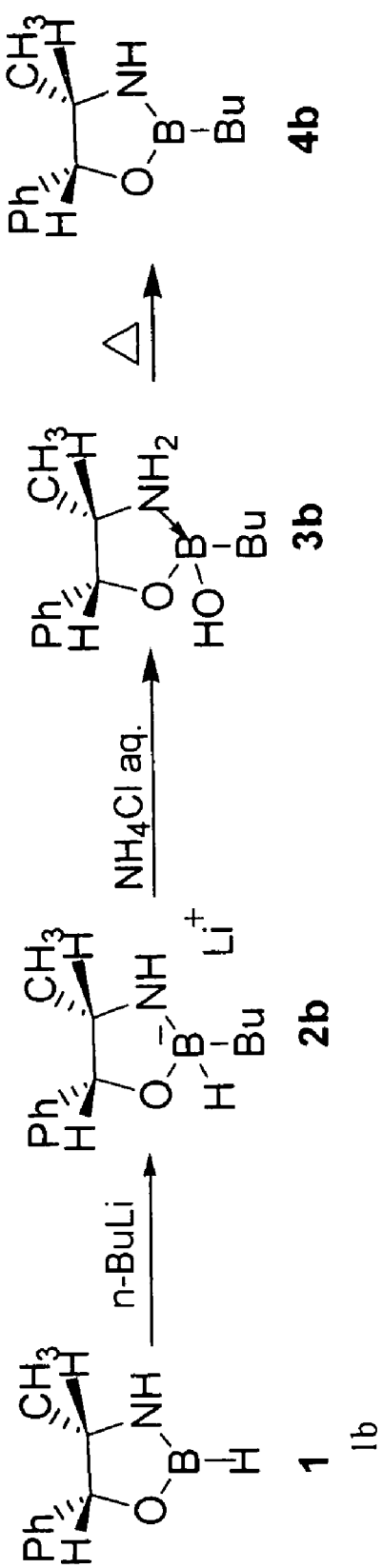
FIG. 2 is a schematic diagram showing one preferred synthesis of 4b. (4S,5R)-B-4-methyl-5-phenyl-[1,3,2]-oxazaborolidine
Figure 3A:
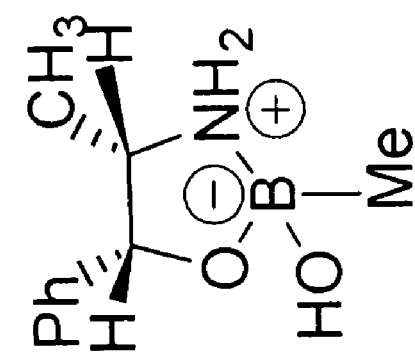
FIG. 3a is a schematic diagram of intermediate, Methyl boronic mono ester of (1R,2S)-2-amino-1-phenyl-propan-1-ol or, of norephedrine, prepared in accordance with synthesis shown in FIG. 2.
Figure 3B:
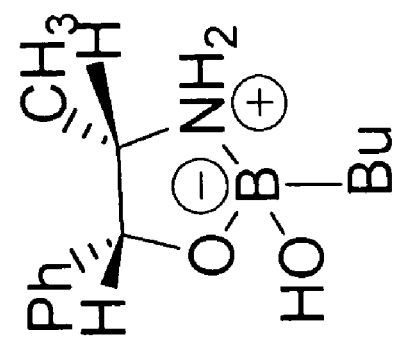
FIG. 3b is a schematic diagram of intermediate, Butyl boronic mono ester of (1R,2S)-2-amino-1-phenyl-propan-1-ol or, of norephedrine, prepared in accordance with synthesis shown in FIG. 2.
Figure 3C:
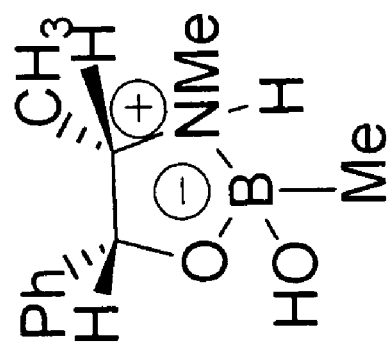
FIG. 3c is a schematic diagram of intermediate, Methyl boronic mono ester of (1R,2S)-2-methylamino-1-phenyl-propan-1-ol or, of ephedrine, prepared in accordance with synthesis shown in FIG. 2.
Figure 3D:
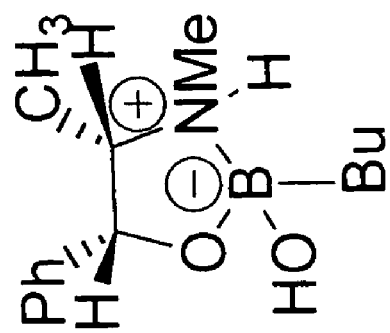
FIG. 3d is a schematic diagram of the intermediate, Butyl boronic mono ester of (1R,2S)-2-methylamino-1-phenyl-propan-1-ol or, of ephedrine, prepared in accordance with synthesis shown in FIG. 2.

With reference to FIG. 2, one preferred method of B-alkylation of an oxazaborolidine is described. The oxazaborolidine 1 is derived from (1R, 2S)(-)-norephedrine by the n-butyllithium addition, forming the corresponding borohydride 2b. After an aqueous work-up, the borate acid 3b was isolated as a clear oil. This intermediate 3b was observed to be remarkably stable to acid and base hydrolysis; it can act as a source for the heterocyclic catalyst. The formation of product 4b was successfully completed by heating neat intermediate 3b, obtaining a 75% yield of the distilled product with more than 95% purity.

Figure 1:
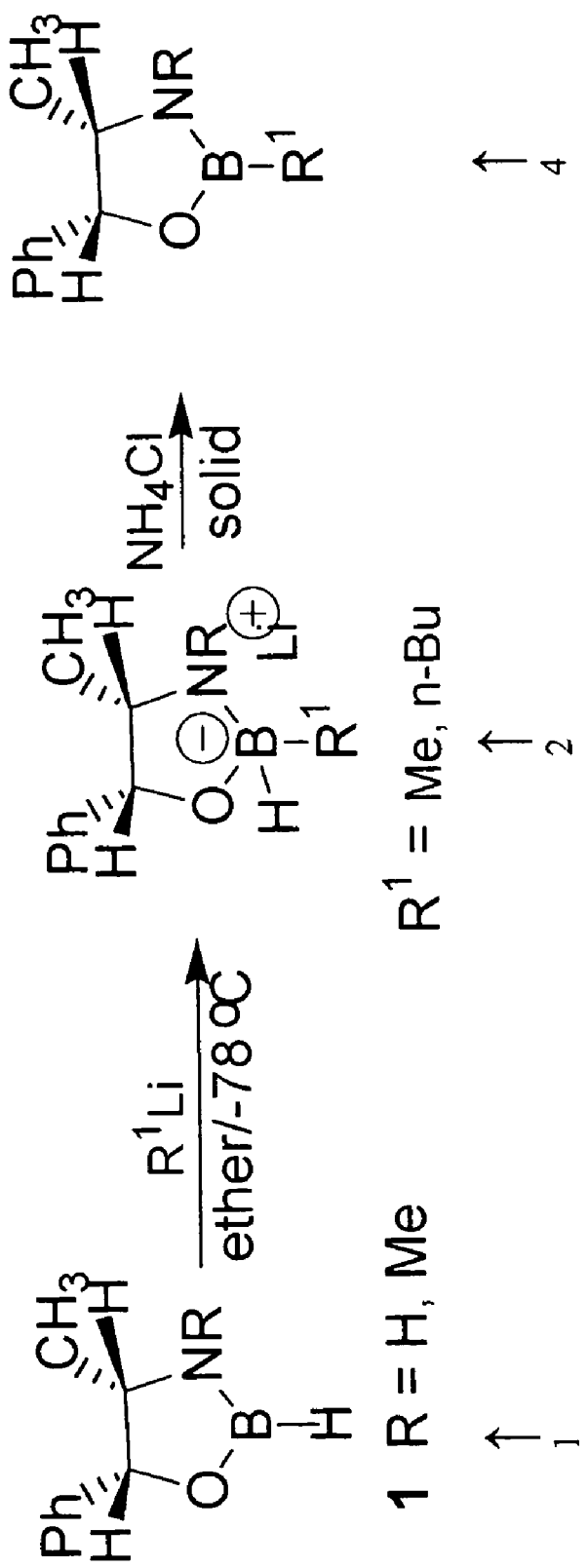
FIG. 1 is a schematic diagram showing one preferred synthesis of pure B-alkyl-1,3,2-oxazaborolidines.

A preferred synthesis procedure according to FIG. 1, follows. To a solution of Borane-THF (43 mmol, 43 mL, 1.0 M) at room temperature was added drop-wise a solution of (1R,2S)(-)norephedrine (2.5 g, 15.5 mmol) in THF (25 mL). After the clear reaction mixture was stirred for 12 hours at room temperature, the solvents were removed under vacuum (20 mmHg) and the white foamy residue was gradually heated in an oil bath to 130° C. and maintained at this temperature for 30 min. A clear crystalline solid compound was obtained, with properties similar to the B—H-1,3,2-oxazaborolidine reported by Quallich in U.S. Pat. No. 6,037, 505, May 14, 2000. A solution of n-BuLi (18.6 mmol, 8.0 mL, 2.32 M in hexanes) was added in 15 minutes to the previously obtained solid dissolved in anhydrous ether (30 mL) and cooled at −78° C. The mixture was stirred overnight at 25° C. The pale rose mixture with a fine suspension was cooled at 0° C. and then allowed to react with solid ammonium chloride (4.4 g, 82.5 mmol) for 4 hours at room temperature. The solid was removed by filtration using a Schlenk filter under nitrogen flow and vacuum (15 mmHg). The filtrated was concentrated using a vacuum pump and heated at 40° C. obtaining the crude product (3.9 g, 99% yield). A short path distillation at reduced pressure furnished the pure B-butyl-1,3,2-oxazaborolidine 4b as a clear oil. Its properties were measured as follows: 2.0 g, 56%, 98% purity by GC/MS; Bp 82° C./0.1 mmHg; IR(v cm$^{-1}$) 3219(NH); B are identified in table 1 for the intermediates shown in FIGS. 3a, 3b, 3c and 3d and the resulting products shown in FIGS. 4a, 4b, 4c and 4d.

TABLE 1

| Int. (FIG. #) | $^{11}$B-NMR (ppm)[a] | Bp. (° C./mmHg) | Yield (%)[b] | Product (FIG. #) | $^{11}$B-NMR (ppm)[a] | Bp. (° C./mmHg) | Yield (%)[c] | Yield (%)[c] |
|---|---|---|---|---|---|---|---|---|
| 3a | 7.1 | 95/0.7 | 80 | 4a | 32 | 42/0.12 | 48[d] | 65[f] |
| 3b | 8.0 |  | 91 | 4b | 35 | 82/0.1 | 75[d] | 56[f] |
| 3c | 8.1 | 120/0.5 | 75 | 4c | 34 | 80/2.0 | 45[d] | 58[f] |
| 3d | 8.5 | 110/0.1 | 97 | 4d | 34 | 84/0.55 | 50[d] | 70[f] |

NMR (500 MHz), δ (CDCl$_3$, ppm) 35; H δ 7.3 (m, 5H), 7.50 (d, J=6 Hz, 1H), 3.9 (m, 1H), 3.48 (br s, 1H, NH), 1.5 (m, 4H), 0.9 (m, 5H), 0.6 (d, J=6 Hz, 3H); C δ 139.6, 127.7, 127.2, 126.7, 126.1, 82.1, 53.8, 27.3, 25.4, 20.4, 13.8, 11.3 (br); MS(m/z): 216.9 (M$^+$), 202 (100%).

Figure 4D:
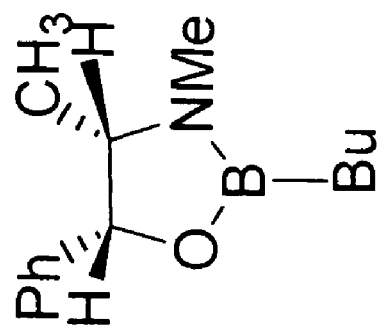
FIG. 4d is a schematic diagram of the product, (4S,5R)-2-Butyl-3,4-dimethyl-5-phenyl-[1,3,2]oxazaborolidine, prepared in accordance with synthesis shown in FIG. 1 and FIG. 2.
Figure 4C:
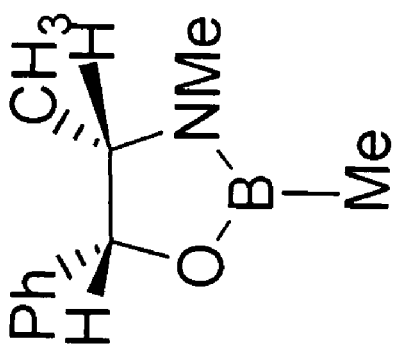
FIG. 4c is a schematic diagram of the product, (4S,5R)-2,3,4-Trimethyl-5-phenyl-[1,3,2]oxazaborolidine, prepared in accordance with synthesis shown in FIG. 1 and FIG. 2.
Figure 4B:
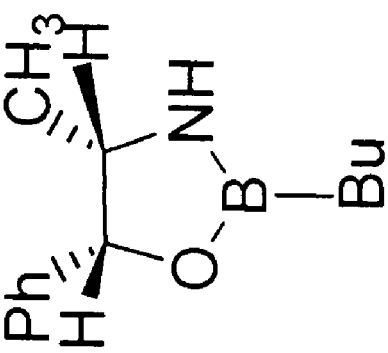
FIG. 4b is a schematic diagram of the product, (4S,5R)-2-Butyl-4-methyl-5-phenyl-[1,3,2]oxazaborolidine, prepared in accordance with synthesis shown in FIG. 1 and FIG. 2.
Figure 4A:
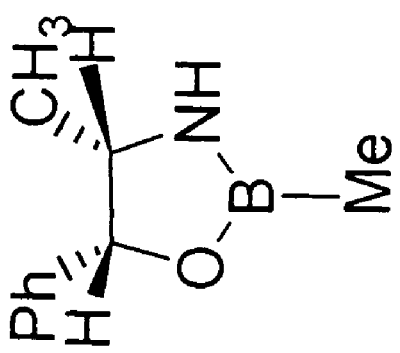
FIG. 4a is a schematic diagram of the product, (4S,5R)-2,4-Dimethyl-5-phenyl-[1,3,2]oxazaborolidine, prepared in accordance with synthesis shown in FIG. 1 and FIG. 2.

With reference to FIGS. 3a–3d and 4a–4d, the synthesis of four B-alkyl-1,3,2-oxazaborolidines is further described. With reference to these figures, the compounds shown in FIGS. 3a–3d illustrate the intermediate product of the synthesis and the compounds shown in FIGS. 4a–4d illustrate the resulting product of the respective intermediate (e.g. the product shown in FIG. 4a is derived from the intermediate shown in FIG. 3a).

The same approach (as described above with reference to FIG. 2) for these synthesis were applied for the preparation of the other B-alkyl 1,3,2-oxazaborolidines derived from (1R, 2S)(-)-norephedrine and (1R, 2S)-(-)-ephedrine, which are shown in FIGS. 4a–4d. In general, the B—H oxazaborolidines were synthesized following the established condensation reaction of the corresponding chiral 1,2-amino alcohol with borane-THF. The boron alkylation with n-butyl-, or methyllithium, of the in situ prepared B—H oxazaborolidine took place readily at -78° C., forming the corresponding lithium borohydride salt 2 (as shown in FIG. 1). Upon treatment with an aqueous ammonium chloride solution, extraction with ether or dichloromethane, and drying the organic phase with sodium sulfate, produced the crude borate acid-amine complexes 3 (also shown in FIG. 1) with high purity and excellent yield. The B-butyl oxazaborolidine derived from norephedrine was obtained in good yield when the borate acid shown in FIG. 3b was heated under reduced pressure during distillation. In the case of analogues shown in FIGS. 3a, 3c and 3d, the yields of the pure B-alkyloxazaborolidines obtained by the same dehydration method were modest, since a significant amount of the intermediate also codistilled with the oxazaborolidine and afterwards the pure intermediates shown in FIGS. 3a, 3c and 3d were obtained. The yields of the desired heterocyclic products were improved by azeotropic distillation using toluene or xylene and 4 Å molecular sieves to remove water. Accordingly, this process is preferred for these compounds.

A nonaqueous direct alternative to prepare the B alkylated oxazaborolidine from the borohydride intermediate 2 (shown in FIG. 1) by treatment with MeI or TMSCl did not yield optimal results. However, the use of anhydrous ammonium chloride provided the expected oxazaborolidines in good yield and with excellent purity as indicated by GC/MS, B, H and C NMR. The B NMR signals and boiling points of intermediates and B-methyl and n-butyl substituted oxazaborolidines, and the isolated yields of the analytical pure compounds prepared by the aqueous and dry methods, With respect to Table 1, the first column identifies the intermediate by reference to the figure in which it is shown. The second column identifies chemical displacements of the respective intermediate using BF$_3$—OEt$_2$ as an internal standard. The third column identifies the boiling point of the intermediate measured in ° C. per millimeter of mercury. The fourth column identifies the crude yield of the intermediate. The fifth column identifies the final product by reference to the figure in which it is shown. The sixth column identifies chemical displacements of the respective product using BF$_3$—OEt$_2$ as an internal standard. The seventh and eight columns identify the yields of isolated products purified by distillation and characterized by their spectral data. The seventh column, in particular, identifies the yield by treatment with aqueous ammonium chloride and calculated by crude product. The eighth column, in particular, identifies the yield by treatment with anhydrous ammonium chloride.

According to a further aspect of the invention, the above methods extend to other B-substituents such as sec-butyl derived from ephedrine and norephedrine. The corresponding oxazaborolidines have been obtained in good yield and with high purity (98%) as clear oils after vacuum distillation. In addition, the methods extend to the alkylation of the B—H oxazaborolidine of norephedrine using organomagnesium (BuMgBr) reagents instead of lithium reagent. This method permits the synthesis of a wide variety of B-alkyl substituents.

In addition, other oxazaborolidines derived from chiral amino alcohols such as, (1S,2R)-1,2-diphenyl-2-aminoethanol(1R,2S)-1,2-amino indanol and (S)∀,∀-diphenyl prolinol have been prepared, in somewhat lower yields, according to the above methods. Finally, in addition to the B-butyl oxazaborolidine derived from (S)-∀,∀-diphenyl prolinol, a dimeric borane complex was isolated.

In summary, the invention achieves the first efficient and general approach to B-alkylated oxazaborolidines derived from ephedrine and norephedrine, by means of a general synthesis mechanism generally applicable to B-substituted oxazaborolidines.

Figure 5:
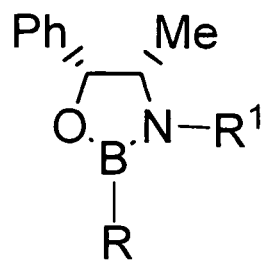
FIG. 5 is a schematic diagram of the products: (a): (4S,5R)-2-sec-Butyl-3-methyl-5-phenyl-[1,3,2]oxazaborolidine, where R=sec-butyl and $R^1$=H; and (b): (4S,5R)-2-sec-Butyl-3,4-dimethyl-5-phenyl-[1,3,2]oxazaborolidine, where R=sec-butyl; $R^1$=Me, prepared in accordance with synthesis shown in FIG. 1.
Figure 6A:
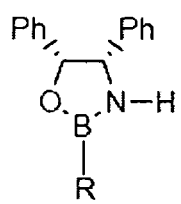
FIG. 6a is a schematic diagram of the product, having a family name of: B-methyl or B-butyl-1-[1,3,2]-oxazaborolidine derived from (1S,2R)-1,2-diphenylethanol, prepared in accordance with synthesis shown in FIG. 1. For R=Me, the specific name is (4S,5R)-2-Methyl-3,5-diphenyl-[1,3,2] oxazaborolidine; For R=Butyl, the specific name is (4S,5R)-2-Butyl-3,5-diphenyl-[1,3,2]oxazaborolidine.
Figure 6B:
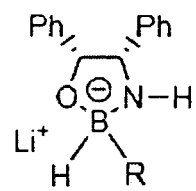
FIG. 6b is a schematic diagram of the product, having a family name of: Lithium borohydrides of B-methyl or B-butyl- of [1,3,2]-oxazaborolidine derived from (1S,2R)-1,2-diphenylethanol, prepared in accordance with synthesis shown in FIG. 1. For R=Me, the specific name is (4S,5R)-2-Methyl-3,5-diphenyl-[1,3,2]oxazaborolidine lithium hydride; For R=Butyl, the specific name is (4S, 5R)-2-Butyl-3,5-diphenyl-[1,3,2]oxazaborolidine lithium hydride.
Figure 7A:
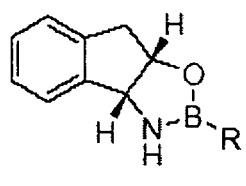
FIG. 7a is a schematic diagram of the product, having a family name of B-methyl or B-butyl-1-[1,3,2]-oxazaborolidine derived from (1R,2RS)-cis-1,2-amino indanol, prepared in accordance with synthesis shown in FIG. 1. For R=Me, the specific name is 2-Methyl-3,3a,8,8a-tetrahydro-2H-1-oxa-3-aza-2-bora-cyclopenta[a]indene. For R=Bu, the specific name is 2-Butyl-3,3a,8,8a-tetrahydro-2H-1-oxa-3-aza-2-bora-cyclopenta[a]indene.
Figure 7B:
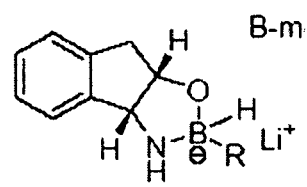
FIG. 7b is a schematic diagram of the product, having a family name of Lithium borohydrides of B-methyl or B-butyl-1-[1,3,2]-oxazaborolidine derived from (1R,2S)-cis-1,2-amino indanol, prepared in accordance with synthesis shown in FIG. 1. For R=Me, the specific name is 2-Methyl-3,3a,8,8a-tetrahydro-2H-1-oxa-3-aza-2-bora-cyclopenta[a]indene lithium borohydride; For R=Bu, the specific name is 2-Butyl-3,3a,8,8a-tetrahydro-2H-1-oxa-3-aza-2-bora-cyclopenta[a]indene lithium borohydride.
Figure 8A:
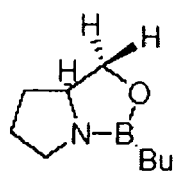
FIG. 8a is a schematic diagram of the product, having a family name of B-butyl of [1,3,2]-oxazaborolidine, derived from (S)-α,α-diphenyl prolinol, prepared in accordance with synthesis shown in FIG. 1. The specific name is (S)-1-Butyl-3,3-diphenyl-tetrahydropyrrolo[1,2-c][1,3,2] oxazaborole.
Figure 8B:
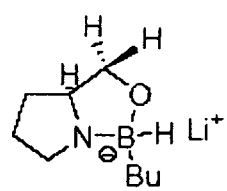
FIG. 8b is a schematic diagram of the product, having a family name of Lithium borohydrides of B-butyl of [1,3,2]-oxazaborolidine derived from (S)-α,α-diphenyl prolinol, prepared in accordance with synthesis shown in FIG. 1. The specific name is (S)-1-Butyl-3,3-diphenyl-tetrahydropyrrolo[1,2-c][1,3,2]oxazaborole lithium hydride.

Specifically, the above method applies to the synthesis of sec-butyl derivatives from ephedrine or norephedrine, as shown in FIG. 5. It also applies to the synthesis of B-methyl or butyl derivatives from (1S,2R)-1,2-diphenyl ethanol, as shown in FIGS. 6a and 6b. It also applies to the synthesis of B-methyl or butyl derivatives from (1R,2S)-1,2-amino indanol, as shown in FIGS. 7a and 7b. Finally it applies to the synthesis of B-butyl derivatives from (S)-alpha, alpha-diphenylprolinol, as shown in FIGS. 8a and 8b.

As shown and described above, the subject invention teaches improved methods for the synthesis of B-alkyloxazaborolidines. These are prepared by B alkylation of the parent heterocyclic compound in accordance with the reaction shown in FIG. 1. Although this synthesis has been described with reference to specific compounds and by use of specific methods, those skilled in the art will appreciate that many variations and modifications are possible without departing from the scope and spirit of the invention. In addition, for purposes of interpreting the following claims, specific reference to a compound or method should be read to encompass not only that specific compound or method but also all equivalent compounds or methods disclosed in the specification or known or which become knowable to those skilled in the art. Accordingly, the following claims should be read to include and to encompass all variations, modifications and equivalents to that which is expressly claimed.

We claim:

1. A method of preparing B-alkylated oxazaborolidines from a parent oxazaborolidine compound comprising the step of alkylating the parent oxazaborolidine compound.

2. The method of claim 1, wherein said method is performed in a single mixing pot.

3. The method of claim 1, further comprising the step of adding an amino alcohol dissolved in a solution of THF to a solution of Borane-THF to form a first solution, mixing the first solution, removing the THF by application of a vacuum, and heating to form the parent oxazaborolidine.

4. The method of claim 3, wherein the amino alcohol comprises norephedrine, wherein the step of heating comprises heating above 120° C., and wherein the parent oxazaborolidine is a crystalline solid.

5. The method of claim 3, wherein the amino alcohol comprises ephedrine, wherein the step of heating comprises heating above 120° C., and wherein the parent oxazaborolidine is an oil.

6. The method of claim 3, wherein the step of alkylating the parent oxazaborolidine compound comprises dissolving the parent oxazaborolidine in a solution of anhydrous ether and adding a solution containing an organolithium to form a second solution.

7. The method of claim 6, wherein the organolithium is selected from the group consisting of n-BuLi, methyllithium, phenyllithium and secbutyllithium.

8. The method of claim 6, wherein the step of alkylating the parent oxazaborolidine further comprises mixing and cooling the second solution.

9. The method of claim 8, wherein the step of alkylating the parent oxazaborolidine further comprises reacting the second solution with solid anhydrous ammonium chloride and filtering the solid anhydrous ammonium chloride out of the second solution.

10. The method of claim 9, wherein the step of alkylating the parent oxazaborolidine further comprises heating the second solution to remove the anhydrous ether from the second solution to form a clear oil, and wherein the clear oil comprises a B-alkylated oxazaborolidine.

11. The method of claim 10, wherein said method is performed in a single mixing pot.

12. The method of claim 3, wherein the step of alkylating the parent oxazaborolidine compound comprises dissolving the parent oxazaborolidine in a solution of anhydrous ether and adding a solution of organomagnesium to form a second solution.

13. A method of B-alkylating an oxazaborolidine comprising the steps of:
providing a parent oxazaborolidine;
performing n-BuLi addition on the parent oxazaborolidine to form the corresponding borohydride; and
reacting the corresponding borohydride with ammonium chloride to yield a B-alkylated oxazaborolidine.

14. A method of producing a B-alkylated oxazaborolidine comprising the steps of:
reacting an amino alcohol with borane to produce a parent oxazaborolidine; and
alkylating the parent oxazaborolidine to produce the B-alkylated oxazaborolidine.

* * * * *